(12) United States Patent
Mantovani et al.

(10) Patent No.: US 7,858,577 B2
(45) Date of Patent: *Dec. 28, 2010

(54) USE OF THE LONG PENTRAXIN PTX3 FOR THE TREATMENT OF DISEASES CAUSED BY AN ALTERED ACTIVATION OF THE GROWTH FACTOR FGF-2

(75) Inventors: Alberto Mantovani, Milan (IT); Barbara Bottazzi, Milan (IT); Marco Presta, Brescia (IT); Marco Rusnati, Brescia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 296 days.

This patent is subject to a terminal disclaimer.

(21) Appl. No.: 10/416,225

(22) PCT Filed: Nov. 8, 2001

(86) PCT No.: PCT/IT01/00563

§ 371 (c)(1), (2), (4) Date: Aug. 28, 2003

(87) PCT Pub. No.: WO02/38169

PCT Pub. Date: May 16, 2002

(65) Prior Publication Data

US 2004/0023879 A1 Feb. 5, 2004

(30) Foreign Application Priority Data

Nov. 8, 2000 (IT) .................. RM2000A0578

(51) Int. Cl.
*A61K 38/00* (2006.01)
(52) U.S. Cl. .................. 514/1.9; 530/350; 514/9.1
(58) Field of Classification Search .................. 530/350; 536/23.1
See application file for complete search history.

(56) References Cited

U.S. PATENT DOCUMENTS 5,426,181 A * 6/1995 Lee et al. .................. 536/23.5

FOREIGN PATENT DOCUMENTS

| WO | 99/32516 A | 7/1999 |
|---|---|---|
| WO | WO 9932516 A2 * | 7/1999 |

OTHER PUBLICATIONS

Janeway, Immunobiology, third edition, 1997, Garland Publishing Inc., p. G1.*
Benharroch et al., Isr J Med Sci, 1990, 26:212-219.*
Jackson et al., Molecular and Cellular Endocrinology, 2006, 247:183-191.*
Korah et al., Cancer Research, 2000, 60:733-740.*
Luchetti et al., Clin Exp Immunol 2000, 119:196-202.*
Rolph et al., Arterioscler Thomb Vasc Biol 2002, 22:1-5.*
Givol et al., FASEB J., 1992, 6:3362-3369.*
Dionne et al., EMBO J., 1990, 9:2685-2692.*
Pels et al., Jnp. Circ. J., 1997, 61:893-904.*
Gewurz et al., Curr. Opin. Immunol., 1995, 7:54-64.*
Bassi et al., Clin Rev Allergy Immunol. Nov. 18, 2008. [Epub ahead of print], 8 pages.*
Bevelacqua et al., Int J Mol Med. Sep. 2006;18(3):415-23.*
Kotooka et al., Atherosclerosis. Mar. 2008;197(1):368-74. Epub Jul. 19, 2007.*
Souza et al., Am J Pathol. Apr. 2009;174(4):1309-18. Epub Mar. 12, 2009.*
Popma et al., Am J Med. Jan. 1990;88(1N):16N-24N.*
Zhang et al., J Lab Clin Med. Aug. 2002;140(2):119-25.*
Post et al., Clin Cardiol. Jun. 2002;25(6):271-8.*
Camozzi et al., Arterioscler Thromb Vasc Biol. Sep. 2000;25(9):1837-42. Epub Jul. 14, 2005.*
Linder et al., Proc Natl Acad Sci U S A. May 1, 1991;88(9):3739-43.*
Rutherford et al., Atherosclerosis. Apr. 1997;130(1-2):45-51.*
Merck Manual of Diagnosis and Therapy, 17$^{th}$ edition, 1999, pp. 729-731.*
Luchetti et al; "Expression and Production of the Long Pentraxin PTX3 in Rheumatoid Arthritis (RA)"; Clinical and Experimental Immunology, vol. 119, Jan. 2000, pp. 196-202, XP002191383.
Polentarutti et al; "Interferon-Gamma Inhibits Expression of the Long Pentraxin PTX3 in Human Monocytes"; European Journal of Immunology, vol. 28, 1998, pp. 496-501, XP002191384.
Bottazzi et al; "Multimer Formation and Ligand Recognition by the Long Pentraxin PTX3"; The Journal of Biological Cahemistry, vol. 272, No. 52, Dec. 26, 1997, pp. 32817-32823, XP002191385.
Introna et al; "Cloning of Mouse PTX3, A New Member of the Pentraxin Gene Family Expressed at Extrahepatic Sites"; Blood, W.B. Saunders, Philadelphia, VA, US, vol. 87, No. 5, Mar. 1, 1996, pp. 1862-1872, XP002113121.
Brooks, P. et al., "Use of the 10-Day-Old Chick Embryo Model for Studying Angiogensis" Methods in Molecular Biology, vol. 129, pp. 25-269. Jul. 1999.
Ribatti, D. et al., "The Chick Embryo Chorioallantoic Membrane as a Model for in vivo Research on Anti-Angiogenesis" Current Pharmaceutical Biotechnology, 2000, pp. 73-82.

* cited by examiner

*Primary Examiner*—Michael Szperka
(74) *Attorney, Agent, or Firm*—Lucas & Mercanti, LLP (57) ABSTRACT

The use of the long pentraxin PTX3 (PTX3) or one of its functional derivatives is described for the preparation of medicament which inhibits the biological activity of the growth factor FGF-2, useful for the prevention and treatment of diseases brought about by an altered activation of said growth factor FGF-2.

21 Claims, 6 Drawing Sheets

USE OF THE LONG PENTRAXIN PTX3 FOR THE TREATMENT OF DISEASES CAUSED BY AN ALTERED ACTIVATION OF THE GROWTH FACTOR FGF-2

This application is the U.S. national phase of international application PCT/IT01/00563 filed 8 Nov. 2001, which designated the US.

The present invention relates to the use of the long pentraxin PTX3 (PTX3) or one of its functional derivatives for the preparation of a medicament which inhibits the biological activity of the growth factor FGF-2, said medicament being useful for the prevention and treatment of diseases brought about by an altered activation of said growth factor FGF-2.

Among the diseases brought about by an altered activation of the growth factor FGF-2 are included diseases provoked by an altered angiogenesis and by an uncontrolled proliferation of fibroblasts or smooth muscle cells.

The first compound endowed with antiangiogenic activity was discovered in the cartilage by Henry Brem and Judath Folkman in 1975 (J. Exp. Med. Feb. 1, 1975;141(2):427-39). The authors thought that this discovery could be used to control pathological process, such as tumor growth, metastasis, chronic and acute inflammation of the joint and diabetic retinopathy, using selective inhibitors of the pathological neoangiogenesis.

Angiogenesis in the adult is normally quiescent, but it represents a normal function, for example in the healing of wounds, or in the reconstruction of the endometrium during the female reproductive cycle.

The angiogenic response is physiologically stimulated when the vascular functions are reduced and tissue perfusion is inadequate.

More generally, it can be claimed that, in physiological conditions, angiogenesis constitutes a positive feedback in response to inadequate perfusion, or to a reduced supply of oxygen and nutrients, such as occurs, for instance, in the case of occlusion of an artery, in situations of tissue mass growth (for example, the neovascularisation that accompanies the formation of muscle tissue); and in the case of an increased work load in association with an increased oxygen and nutrient requirement.

It is well known that the growth of a primary tumor is favoured by good vascularisation of the tumor tissue. An adequate supply of oxygen and nutrients promotes rapid growth of the tumor itself.

It has been demonstrated that the extent of angiogenesis can be an extremely negative factor in the prognosis of neoplasms (van Hinsbergh V W, Collen A, Koolwijk P; Ann. Oncol., 10 Suppl., 4:60-3, 1999; Buolamwini J K; Curr., Opin., Chem., Biol., 3(4):500-9, August 1999).

It is also known, in the tumor field, that a fundamental stage in the biology of the tumor cell is the acquisition of metastasising capability.

The tumor cells that metastasise are able to lose adherence to the surrounding structures, invade blood and lymphatic vessels and colonise other tissues at a distance where they can continue to reproduce themselves.

Metastasising is also a critical event in the clinical history of the disease, being the main cause of death due to cancer. It is closed associated with and facilitated-by the presence of vascular tissue in the tumor site or adjacent areas.

The migration of tumor cells across the surrounding structures enables the cells to reach the intra-tumor blood vessels, whether pre-existing or formed by neo-angiogenesis, and thus reach the bloodstream (Ray J M., Stetler-Stevenson W G; Eur. Respir. J., 7(11):2062-72, 1994; Stetler-Stevenson W G, Liotta L A, Kleiner D E Jr; FASEB J., 7(15):1434-41, December 1993).

The presence of communication between lymphatic and blood vessels in the vascular region of the tumor enables the neoplastic cells to move in both vascular systems.

Recent studies have shown a direct relationship between angiogenesis and arthritic disease (Koch A E; Arthritis and Rheumatism 41:951-962, 1998). In particular, it has been demonstrated that neo-vascularisation of the articular cartilages plays a crucial role in pannus formation and in progression of arthritis. A normal cartilage does not possess blood vessels, while the synovial fluid of arthritic patients contains an angiogenesis-stimulating factor produced by endothelial cells (EASF).

The presence of this factor is associated with vascularisation and degradation of the cartilage.

Other diseases are also related to abnormal angiogenesis.

It has been found that, in diabetic retinopathy [Histol Histopathol. October 1999; 14(4): 1287-94], psoriasis [Br J Dermatol. December 1999; 141(6):1054-60], chronic inflammation and arteriosclerosis [Planta Med December 1998; 64(8): 686-95], neovascularisation of the affected tissues is a facilitating factor.

The growth factor FGF-2 is a cationic polypeptides of 18 kDa capable both of inducing neoangiogenesis in vivo and cells proliferation, chemotaxis and production of proteases in endothelial cells in culture (Basilico and Moscatelli, 1992, Adv. Cancer Res. 59:115-65).

The role of FGF-2 in the tumoral angiogenesis is already known (Pathol. Biol. (Paris) April 1999; 47(4):364-7).

In J. Pathol. September 1999; 189(1):72-8 is reported that an increased expression of FGF-2, in patients suffering from mesotelioma, is related to an higher aggressiveness and higher mortality of patients affected by such tumoral disease.

In Oncogene Nov. 18, 1999;18(48):6719-24 is reported that FGF-2 confers metastasising propriety to rat bladder carcinoma cells.

Int. J. Cancer May 5, 1999;81(3):451-8 reports that FGF-2 has a strong mitogenic activity, and is involved in the development of human tumors and in the increases of their malignity.

For the cure of tumoral diseases the antiangiogenic therapy respect to the standard traditional chemotherapy presents the following advantages (Cancer Research 1998, 58, 1408-16):
1. Higher specificity: it has as target the tumor neovascularisation process;
2. Higher biodisponibility: it has as target the endothelial cells, easy reachable without the problems linked to the traditional chemotherapeutic approach which act directly on the tumoral cells;
3. Minor chemoresistence: this may be the most important advantage of this therapy; in fact, being the endothelial cells, respect to the tumoral cells, genetically stable, phenomenon of drug resistance are improbable;
4. Minor metastasising: the blockage of the neovascularisation limits the propagation of the tumor cells in the other parts of the body through the bloodstream;
5. The apoptosis is favoured: the blockage of the vascular net in the tumor decrease the oxygen and nutrient availability for the tumoral cells, in this way the apoptosis is increased;
6. Reduction of the systemic toxicity: toxic effect, such as mielosuppression, gastrointestinal effects and transient alopecia, present with the traditional chemotherapy, are not observed with the antiangiogenic therapy.

To determinate these effects FGF-2 reacts with two different receptor classes present on target cells surfaces: the receptors having high affinity endowed with tirosin kinases activity (FGFRs) and receptors endowed with low affinity represented by proteoglycan eparan sulfate (HSOGs) (Johnson and Williams, 1993, Adv. Cancer Res. 60:1-41; Moscatelli, 1987, J. Cell. Physiol. 131:123-30).

FGF-2 is a potent mitogen for medial smooth muscle cells and is necessary for their proliferation after balloon catheter injury (J. Biol. Chem. Apr. 14, 2000; 275 (15): 11270-7).

Therefore, diseases caused by an altered activation of the growth factor FGF-2 also include the hyperplasia of the muscular wall of the arteries that occurs during restenosis after angioplastic or "coronary stenting" [J. Vasc. Surg. February 1997; 25(2):320-5].

The control of FGF-2 dependent neovascularisation represents one of the fundamental elements for the control and cure of diseases linked to an altered angiogenesis, as well as the control of FGF-2-dependent uncontrolled proliferation of fibroblasts or SMCs is crucial for the treatment of cicatrization linked to excessive fibroblastic response and restenosis after angioplastic.

The availability of new therapeutical compound which specifically inhibit the biological activity of FGF-2 is an objective of primary importance for the prevention and treatment of diseases brought about by an altered activation of this growth factor. Such diseases include arthritic disease, tumor, tumor metastasis, diabetic retinopathy, psoriasis, chronic inflammation, arteriosclerosis, cicatrization linked to excessive fibroblastic response and restenosis after angioplastic.

PTX3 is expressed in various cell types (Bottazzi et Al., J., Biol. Chem. 1997, 272: 32817-32823) particularly in mononuclear phagocytes and endothelial cells, after exposure to the inflammatory cytokines Interleukin 1β (IL-1β) and Tumor Necrosis Factor alpha (TNF-α).

To date, the biological function of PTX3 has not yet been fully understood.

PTX3 consists of two structural domains, a N-terminal domain unrelated to any known molecule, and a C-terminal domain similar to the short pentraxins such as C-reactive protein (CRP) (Breviario F., et al., J. Biol. Chem. 267:22190, 1992).

A substantial degree of similarity has been found between human PTX3 (hPTX3) and animal PTX3s. In particular, mouse PTX3. (mPTX3) is very similar to hPTX3 in terms of DNA sequence and gene organisation and location. The degree of identity between human and murine PTX3 gene is 82%, and reaches 90% if conservative substitutions are considered (Introna M., et al.: Blood 87 (1996) 1862-1872). The murine PTX3 gene is located on chromosome 3 of the mouse in a region similar to the human 3q region (q24-28), in agreement with the documented location of hPTX3 in the 3q 25 region (Introna M., et al.: Blood 87 (1996) 1862-1872).

The high degree of similarity between hPTX3 and mPTX3 sequences is a sign of the high degree of conservation of pentraxins during evolution (Pepys M. B., Baltz M. L.: Adv. Immunol. 34:141, 1983).

For a review about pentraxins see H. Gewurz et al, Current Opinion in Immunology, 1995, 7:54-64.

The international application WO99/32516, filed in the name of the applicant, describes the use of the long pentraxin PTX3 for the treatment of infective diseases, inflammatory or tumoral. The anti-tumor activity shown by PTX3, described in WO99/32516, is mediated by the leucocitary recruitment, i.e. on immunologic bases. In WO99/32516 it is never described or suggested the use of PTX3 as useful agent for the treatment of diseases associated with an altered activation of the growth factor FGF-2.

U.S. Pat. No. 5,767,252 describes a neuronal growth factor belonging to the pentraxin family (see also the references there cited). This patent refers to the neurobiology sector.

It has now been found that the long pentraxin PTX3 is capable to bind the FGF-2 with high affinity and specificity. The binding of PTX3 with FGF-2 ($K_d$=8-16 nM) prevents the binding of the latter to its high affinity tyrosine-kinase receptors, and the binding at the site of low affinity receptors, represented by the eparan-sulphate proteoglycans, present on the cell surface. The inhibition of the binding causes an inhibition of the FGF-2 biological activity.

The interaction between FGF-2/PTX3 depends on a correct conformational structure of the growth factor, not only on its basic nature, since PTX3 does not bind the cytocrome C (a protein that share with the FGF-2 molecular weight (18 kDa) and isoelectric point (pH 9.6)).

Moreover, the C-reactive protein, homologous to PTX3, does not bind FGF-2.

Is therefore object of the present invention the use of the long pentraxin PTX3 or a derivatives thereof, or its domain, for preparing a medicament for the prevention and cure of diseases which are counteracted by the inhibition of the biological activity of the growth factor FGF-2.

A further object of the present invention is the use of the long pentraxin PTX3 or a derivatives of the PTX3 or its domain, for preparing a medicament for the prevention and cure of diseases brought about by an altered activation of the growth factor FGF-2. A further object of the present invention is the use of the long pentraxin PTX3 or a derivative thereof, or its domain, for preparing a medicament for the prevention or cure of diseases brought about by an altered angiogenesis, in which the altered angiogenesis is provoked by an altered activation of the growth factor FGF-2, example of said diseases are: arthritic disease, tumor metastasis, diabetic retinopathy, psoriasis, chronic inflammation, arteriosclerosis or tumor, in which the tumor is, for example, sarcoma, carcinoma, carcinoid, bone tumor or neuroendocrine tumor.

A further object of the present invention is the use of the long pentraxin PTX3 or a derivatives of the PTX3 or its domain, for preparing a medicament for the treatment of diseases associated with uncontrolled FGF-2-dependent proliferation of fibroblasts or smooth muscular cells, such as the cicatrization linked to excessive fibroblastic response, and the restenosis after angioplastic.

The compound according to the invention is suitable to be used for the inhibition of FGF-2 activity in target cells not only when it is administered as recombinant protein, but also when it is administered endogenously in consequence of the gene transfer of its cDNA.

Is therefore a further object of the present invention the use of cDNA full length of human PTX3 or its derivative or its domain, for preparing plasmidic or viral expression vectors comprising said cDNA, for the gene therapy of diseases caused by an altered activation of the growth factor FGF-2, in which the diseases are, for example, tumor, tumor metastasis, cicatrization linked to excessive fibroblastic response or restenosis after angioplastic.

For "long pentraxin PTX3" is intended any long pentraxin PTX3, independently from its origin natural (human or animal) or synthetic.

For derivatives is intended any functional analogous of the long pentraxin PTX3 as above defined that bear at least a mutation, maintaining its functional capacity to selectively inhibit the FGF-2.

The preferred long pentraxin PTX3 is the human PTX3, which sequence is described in WO99/32516.

The long pentraxin PTX3 described herein can also be used in combination with one or more anticancer drugs for the treatment of tumor diseases in which the increased expression of FGF-2 provokes an higher aggressiveness of the tumor disease, or an higher metastasising capability.

In fact, it is well known that, to avoid the unwanted side effects maintaining the same therapeutic efficacy, most oncological patients are treated not with a single anticancer drug, but with a combination of several anticancer agents or with a combination of anticancer agents in association with antiangiogenic compounds.

The mechanism of action of the more usual anticancer drugs is completely different from the mechanism of action of the compound according to the present invention, in fact, the usual anticancer drugs are cytotoxic vs tumoral cells.

The compound according to the present invention having a different mechanism of action, exert a curative effect (adjuvant effect) additional to the effect exerted by the anti-tumor drug to which it is associated.

It is therefore a further object of the invention described herein the combination of the long pentraxin PTX3 with one or more known anticancer drugs.

A further object of the invention described herein is a pharmaceutical composition containing the long pentraxin PTX3 in combination with one or more known anticancer drugs, such as alkylating agents, topoisomerase inhibitors, antitubulin agents, intercalating compounds, anti-metabolites, natural products such as vinca alkaloids, epipodophyllotoxins, antibiotics, enzymes, taxans, and cyto-differentiating compounds, and one or more excipients or vehicles pharmacologically acceptable.

A further object of the invention described herein is the use of the long pentraxin PTX3, in combination with one or more known anti-tumor compounds, for preparing a medicament for the treatment of tumor, in which the increased expression of FGF-2 provokes an higher aggressiveness of the tumor.

A further object of the invention described herein is the use of the long pentraxin PTX3, in combination with one or more known anti-tumor compounds, for preparing a medicament for the prevention of the onset of tumor metastasis, in which the increased expression of FGF-2 provokes an higher metastasising capability.

A further object of the invention described herein is the use of the long pentraxin PTX3 in combination with, the anticancer compound, for preparing a medicament for the treatment of tumor, characterised in that the long pentraxin PTX3 is present as adjuvant of the anticancer compound.

The following examples illustrate the invention.

EXAMPLE 1

Capacity of PTX3 to Bind FGF in Solution.

This experiment has been performed in order to evaluate PTX3 binding to FGF-2. PTX3 has been produced as described by Bottazzi et al., 1997, J. Biol. Chem. 272:32817-32823. Human recombinant FGF-2 has been produced as described by Isacchi A. et al., Proc. Natl. Acad. Sci. U.S.A. (1991), 88:2628-32. When necessary, FGF-2 has been labelled with $^{125}$I following the method described by Isacchi et al. (see below).

Experimental Procedure

Figure 1:
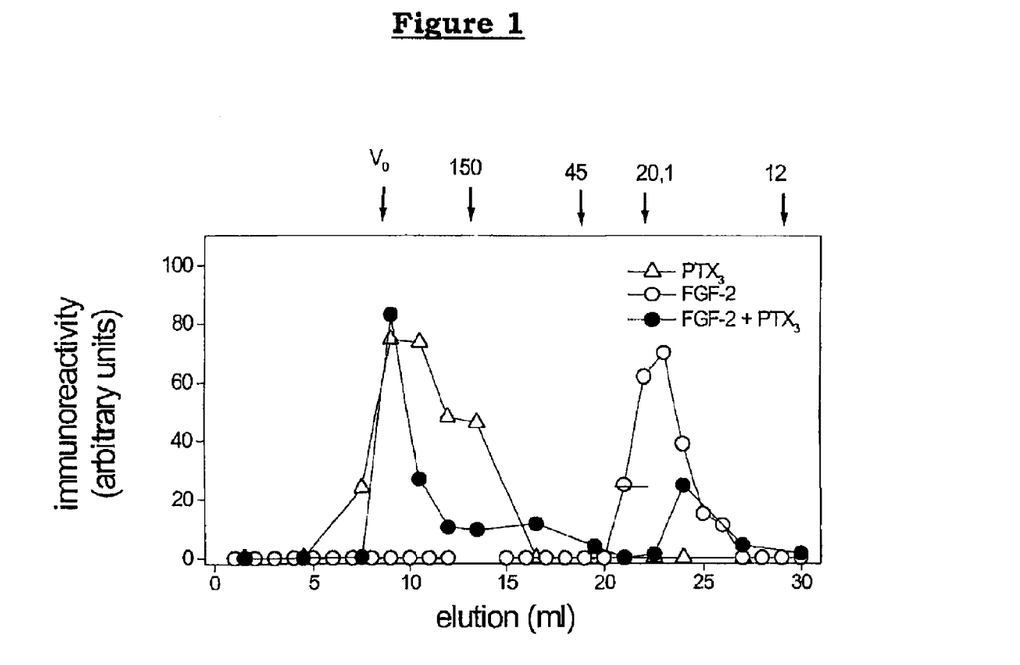
FIG. 1 show that FGF-2 (18.000 D) is eluted from the column with a retention volume of approximately 22 ml.

100 µl of PBS containing 1 µg of FGF-2, (or alternatively 1 µg of PTX3) were chromatographed on a size exclusion fast protein liquid chromatography Superose 12 column (Pharmacia): this column is able to separate proteins depending on their molecular weight. The column was eluted with PBS at a flow rate equal to 1 ml/minute and 1 ml fractions were collected and analyzed by dot, blot with specific antibodies for the two proteins. In order to evaluate PTX3 binding to FGF-2 the two proteins (5 g and 1 µg, respectively), were mixed in 100 µl PBS and incubated at 4° C. for 10 min. before loading onto the column. Fractions were collected and analysed by dot-blot with anti FGF-2 specific antibodies. The results reported in FIG. 1 show that FGF-2 (18.000 D) is eluted from the column with a retention volume of approximately 22 ml. In the same conditions PTX3 (450.000 D) is eluted with the void volume of the column (7 ml.) When FGF-2 pre-incubated with PTX3 for. 10 min. at 4° C. was loaded onto the column, a change in its chromatographic behaviour was observed: in this experimental conditions FGF-2 was eluted from the column with a retention volume equal to PTX3 alone.

EXAMPLE 2

Capacity of Biotinylated PTX3 to Bind Plastic Immobilised FGF-2

100 µl of NaHCO$_3$ pH 9.6 containing 500 ng of FGF-2 or of the complement component C1q were incubated 18 h at 4° C. in 96 wells plastic plates. At the end of incubation wells were washed 3 times with PBS and subsequently incubated 2 h at room temperature with 200 µl of PBS containing 1 mg/ml of Bovine Serum Albumin (BSA). At the end of incubation wells were washed again 3 times with PBS and incubated with 30 ng/ml of $^{125}$I-FGF-2 in presence of increasing amounts of biotinylated PTX3 in 100 µl of PBS (2 h at room temperature).

Figure 2:
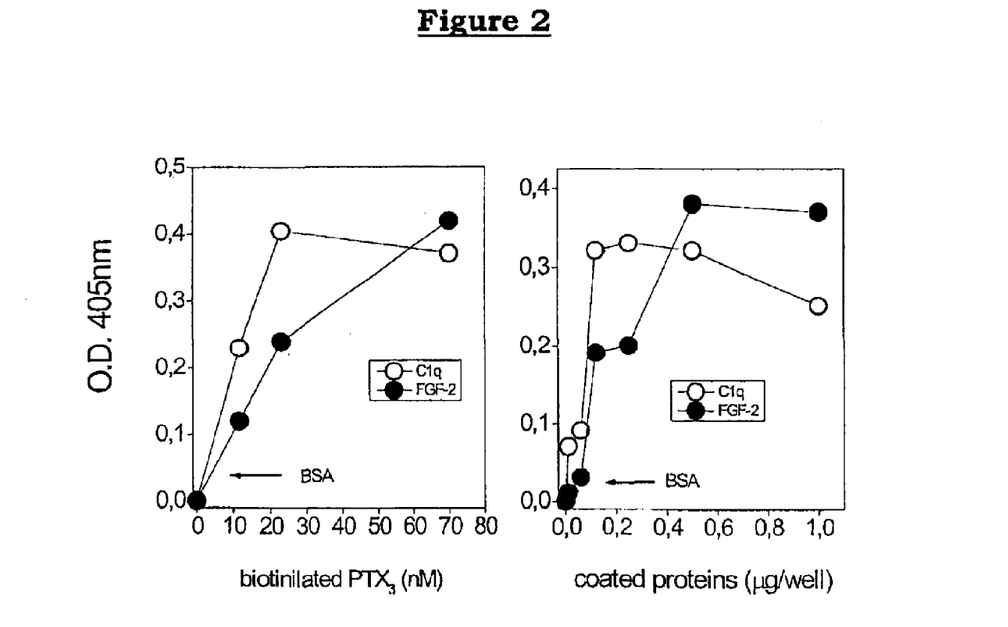
FIG. 2 demonstrates that FGF-2 immobilised on plastic wells is able to bind biotinylated PTX3 in a way similar to the physiologic PTX3 ligand Clq.

Alternatively wells were adsorbed with increasing doses of FGF-2 or C1q and incubated with 100 ng/ml of biotinylated PTX3 in 100 µl of PBS. After this incubation wells were washed 3 times with PBS and incubated 1 h at room temperature with 100 µl of streptavidin HRP conjugate (½₀₀₀). Reaction was developed by adding the chromogen microwell peroxidase substrate system ABTS (Kirkegaard & Perry Laboratories). Plates were read in an automatic ELISA reader at 405 nm. Results reported in FIG. 2 demonstrate that FGF-2 immobilised on plastic wells is able to bind biotinylated PTX3 in a way similar to the physiologic PTX3 ligand C1q (Bottazzi B. et al., 1997, J. Biol. Chem. 272:32817-32823).

EXAMPLE 3

Figure 3:
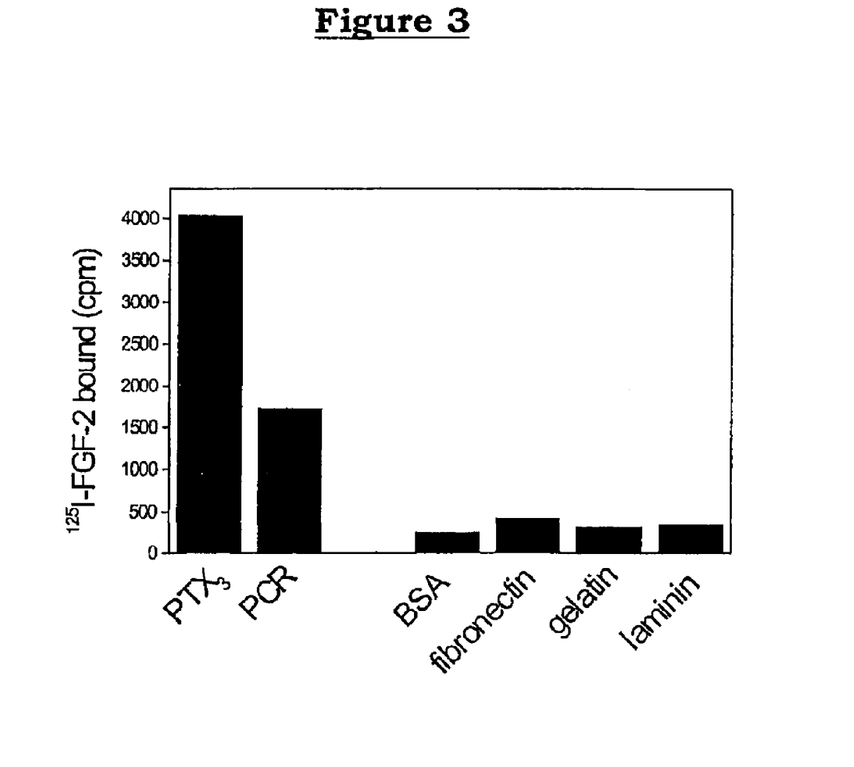
FIG. 3 shows that FGF-2 binds plastic immobilised PTX3 and that this binding is specific since FGF-2 reacts poorly with CRP and does not react with other immobilised proteins.

Characterisation of PTX3-FGF-2 Interactions 96 wells plates were coated at 4° C. with 100 µl of NaHCO$_3$ pH 9.6 containing PTX3 or C reactive protein (200 nM) or alternatively 2 µg/ml of the following proteins used as negative control: bovine serum albumin, fibronectin, gelatine or laminin. After incubation, wells were washed 3 times with PBS and blocked 2 h at room temperature with 200 µl of 1 mg/ml of BSA in PBS. At the end of incubation wells were washed 3 times with PBS and subsequently incubated with 30 ng of $^{125}$I-FGF-2 for 2 h at room temperature. Wells were subsequently washed 3 times with PBS and bound $^{125}$I-FGF-2 was recovered by washing each well twice with 200 µl of 2% SDS in water. Levels of $^{125}$I-FGF-2 were measured in a gamma counter. Results reported in FIG. 3 shows that FGF-2 binds plastic immobilised PTX3 and that this binding is specific since FGF-2 reacts poorly with CRP and does not react with other immobilised proteins.

EXAMPLE 4

$^{125}$I-FGF-2 Binding to Plastic Immobilised PTX3 in the Presence of an Excess of Cold FGF-2

Figure 4:
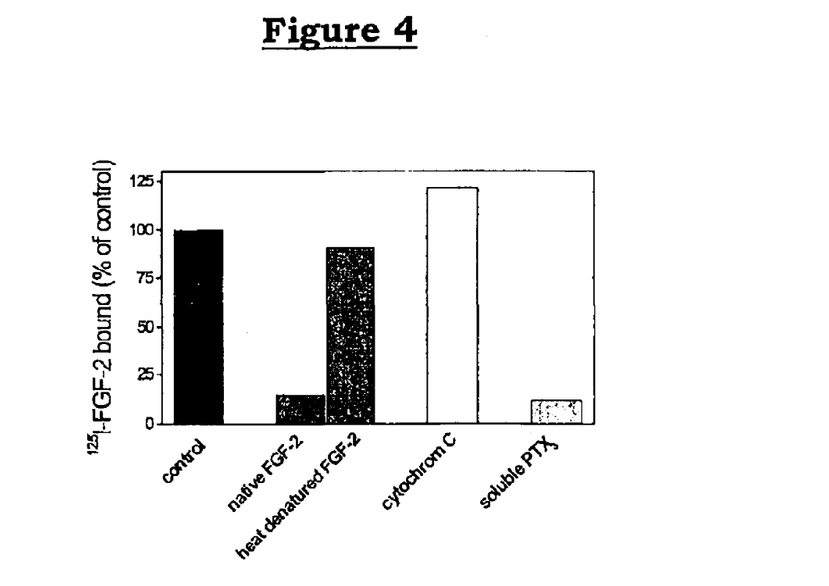
FIG. 4 demonstrates that cold FGF-2 and soluble PTX3 inhibited the interaction between $^{125}$I-FGF-2 and plastic immobilised PTX3.

In a second set of experiments the binding of $^{125}$I-FGF-2 to plastic immobilised PTX3 has been tested in the presence of an excess of both native or heat denatured cold FGF-2 (100 nM), in the presence of similar Cytochrome C concentrations or in the presence of an excess of soluble PTX3 (300 nM). The experiment was performed as described above: The results reported in FIG. 4 demonstrate that cold FGF-2 and soluble PTX3 inhibited the interaction between $^{125}$I-FGF-2 and plastic immobilised PTX3. The observation that heat-inactivated FGF-2 and Cytochrome C (having the same molecular weight and isoelectric point as FGF-2) are not able to bind PTX3 suggests that a correct conformation of the growth factor rather than its basic nature is involved in its capacity to bind PTX3.

EXAMPLE 5

Dissociation Constant (Kd) of FGF-2/PTX3 Interaction

Figure 5:
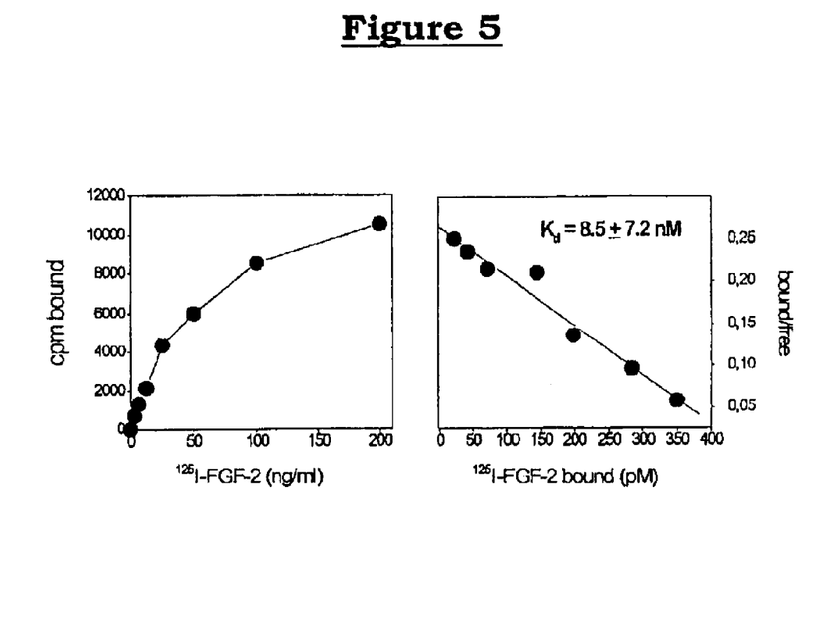
FIG. 5 demonstrates that FGF-2 binds PTX3 in a saturable way and with elevated affinity (Kd =8-16 nM).

With this experiment the dissociation constant (Kd) FGF-2/PTX3 interaction has been determined. For this purpose increasing doses of $^{125}$I-FGF-2 were incubated with plastic immobilised PTX3 and binding results were analysed by Scatchard plot. Results reported in FIG. 5 demonstrate that FGF-2 binds PTX3 in a saturable way and with elevated affinity (Kd=8-16 nM). This affinity is similar to the affinity previously calculated for the interaction of PTX3 with its physiological ligand C1q.

EXAMPLE 6

Effect of PTX3 on FGF-2 Binding to Endothelial Cells

Figure 6:
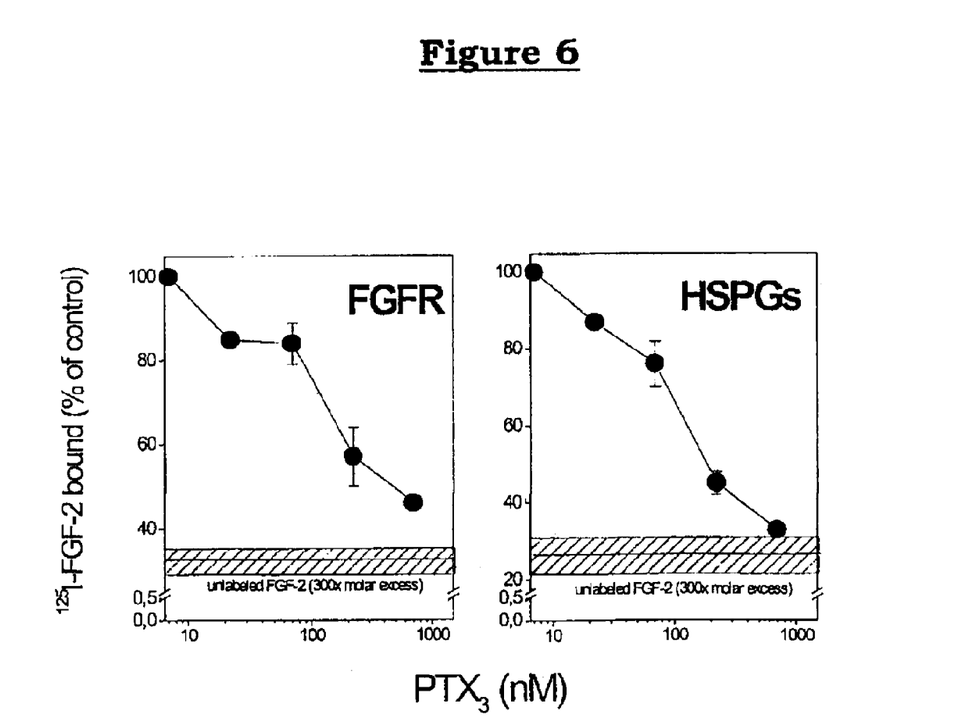
FIG. 6 shows that PTX3 is able to inhibit in a dose-dependent manner the binding of FGF-2 to its high-and low-affinity receptors on endothelial cells.

Transformed foetal bovine aortic endothelial cells GM7373 were seeded at 80,000 cells/cm$^2$ in 24-well dishes in Eagle's minimal essential medium (Eagle's MEM) containing 10% FCS. After 24 h at 37° C. adherent cells were washed twice with Eagle's MEM without FCS and subsequently incubated for 2 h at 4° C. with $^{125}$I-FGF-2 (10 ng/ml) in Eagle's MEM containing 0.15% gelatine and 20 mM HEPES pH 7.5 in the absence or in the presence of increasing concentrations of PTX3. At the end of incubation the amount of $^{125}$I-FGF-2 bound to low (HSPGs) and high affinity receptors (FGFR) was evaluated as described by Moscatelli, 1987 J. Cell. Physiol. 131:123-30. Briefly cells were rinsed twice with 2 M NaCl in 20 mM HEPES buffer (pH 7.5) to remove $^{125}$I-FGF-2 bound to low-affinity binding sites and twice with 2 M NaCl in 20 mM sodium acetate (pH 4.0) to remove $^{125}$I-FGF-2 bound to high-affinity binding sites. Non-specific binding was measured in the presence of a 100-fold molar excess of unlabeled FGF-2 and subtracted from all the values. Results reported in FIG. 6 shown that PTX3 is able to inhibit in a dose-dependent manner the binding of FGF-2 to its high- and low-affinity receptors on endothelial cells.

EXAMPLE 7

Effect of PTX3 on Mitogenic Activity Exerted by FGF-2 on Endothelial Cells

Figure 7:
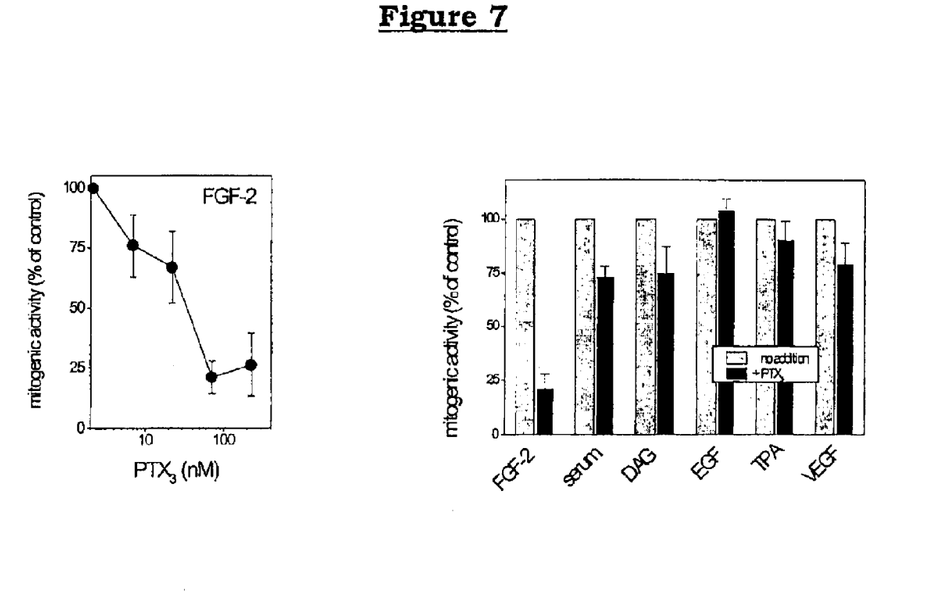
FIG. 7 shows that PTX3 inhibits the mitogenic activity exerted on endothelial cells by FGF-2 in a dose-dependent manner with an $ID_{50}$ equal to 30 nM.

GM 7373 cells were seeded at 75,000 cells/cm$^2$ in 48-well plates in Eagle MEM containing 10% FCS. After 24 h at 37° C. adherent cells were washed twice with Eagle's MEM without FCS and subsequently incubated for 24 h at 37° C. in Eagle's MEM containing 0.4% FCS in the absence or in the presence of FGF-2 (10 ng/ml) and increasing concentrations of PTX3. At the end of incubation cells were trypsinized and counted. In a different set of experiments GM 7373 cells were treated as described above in the presence of different mitogenic stimuli: 10% FCS; 5 µg/ml dyacyl-glycerol (DAG); 10 ng/ml phorbol ester (TPA) 30 ng/ml epidermal growth factor (EGF) or 30 ng/ml vascular endothelial growth factor (VEGF). Results reported in FIG. 7 shown that PTX3 inhibits the mitogenic activity exerted on endothelial cells by FGF-2 in a dose-dependent manner with an ID$_{50}$ equal to 30 nM. This value is similar to the Kd calculated for the interaction FGF-2-PTX3. These results suggest that the inhibition of FGF-2 biological activity by PTX3 is due to its sequestration in extracellular sites. The inhibitory activity of PTX3 on FGF-2 is specific since it is not detectable when other mitogens are used to induce, cellular proliferation.

EXAMPLE 8

Figure 8:
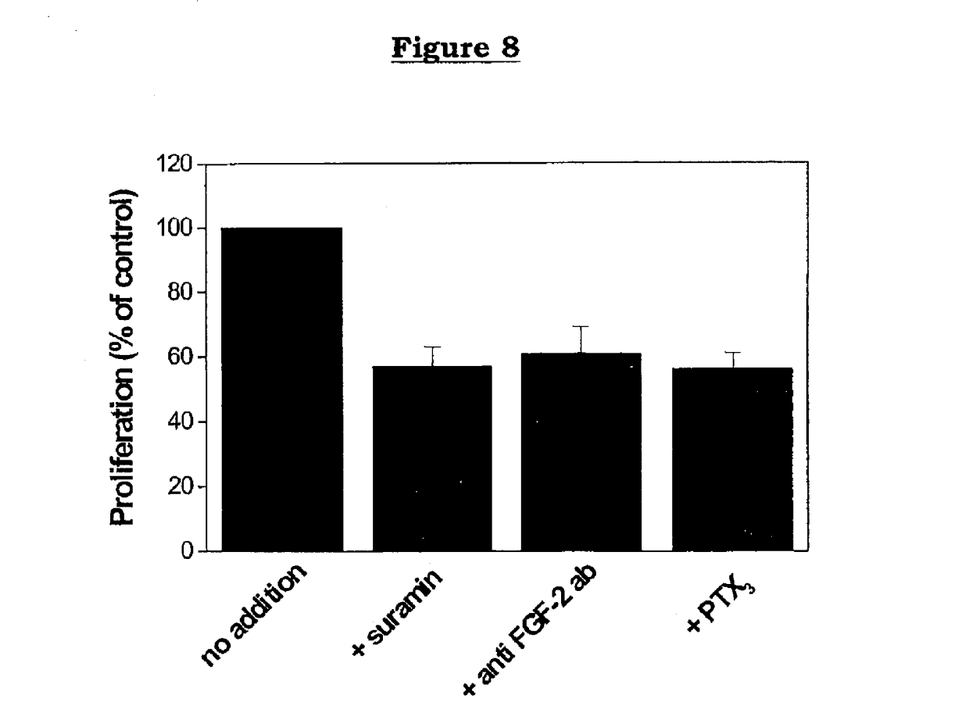
FIG. 8 shows that PTX3 is able to block the autocrine loop of stimulation induced by FGF-2 in MAE3F2T cells, inhibiting their FGF-2 dependent proliferation, in a manner similar to that exerted by anti FGF-2 antibodies and suramin.

Effect of PTX3 on the Proliferation of Transformed Foetal Bovine Aortic Endothelial Cells In this experiment we have investigated the effect of PTX3 on the proliferation of the murine aortic endothelial cell line MAE3F2T stably transfected with an expression vector coding for FGF-2 (Gualandris et al. 1996, Cell Growth Diff. 7:147-60). These cells can proliferate in response to a autocrine loop of stimulation induced by endogenous FGF-2 (Gualandris et al. 1996, Cell Growth Diff. 7:14760). MAE3F2T cells were seeded at 10,000/cm$^2$ in 48-well plates in Dulbecco medium (DMEM) added with 10% FCS. After 24 h at 37° C., adherent cells were washed twice with DMEM without FCS and incubated for 72 at 37° C. in DMEM containing 0.4% FCS in the presence or not of PTX3 (70 nM), anti FGF-2 specific antibodies or suramin (50 µg/ml). Suramin is known for its capacity to sequestrate extracellular FGF-2 and inhibits its biological activities (Rusnati et al., 1996, Mol. Biol. Cell. 7:369-381). At the end of incubation cells were trypsinized and counted in a Burker chamber. Results reported in FIG. 8 shown that PTX3 is able to block the autocrine loop of stimulation induced by FGF-2 in MAE3F2T cells, inhibiting their FGF-2 dependent proliferation, in a manner similar to that exerted by anti FGF-2 antibodies and suramin.

EXAMPLE 9

Effect of PTX3 onto the Neovascularization Induced in vivo by FGF-2

Figure 9:
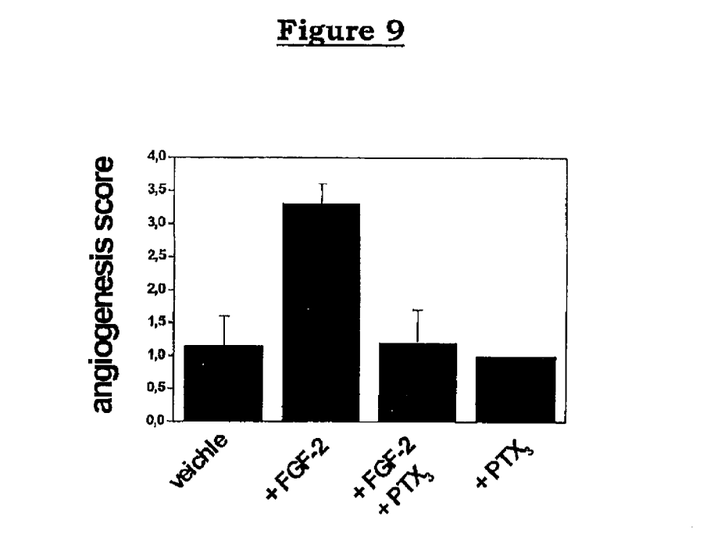
FIG. 9 shows that PTX3 is able to block the neovascularization induced in vivo by FGF-2.

The antiangiogenic potential of PTX3 was evaluated in vivo in the chick embryo chorioallantoic membrane (CAM) assay. Briefly, a window was opened in the egg shell of 3 day-old fertilized chicken eggs. At day 8, gelatin sponges were implanted on the CAMs and adsorbed with 10 ul of PBS alone or containing FGF-2 (at 500 ng/sponge) in the absence or in the presence of PTX3 (5 ug/sponge) (5-6 embryos per group). After 4 days, CAMs were observed in ovo under a Zeiss SR stereomicroscope and the angiogenic response was scored by two investigators without knowledge of the samples tested and graded on an arbitrary scale of 0-4+, with 0 representing no angiogenic response and 4+ representing the strongest activity. Results reported in FIG. 9 shown that PTX3 is able to block the neovascularization induced in vivo by FGF-2.

EXAMPLE 10

Gene Therapy with PTX3

Murine endothelial cells overexpressing FGF-2, named FGF2MAE3F2T (Gualandris et al. 1996, Cell Growth Diff. 7:147-60) were transfected with human PTX3 full length cDNA subcloned in the commercial expression vector pLXSH (Clontech).

In vitro studies on the transfected cell lines obtained were, performed to study the effect of PTX3 over-expression on FGF-2-dependent proliferation of FGF2MAE3F2T cells and their invasive behaviour on three-dimensional fibrin gels.

Figure 10:
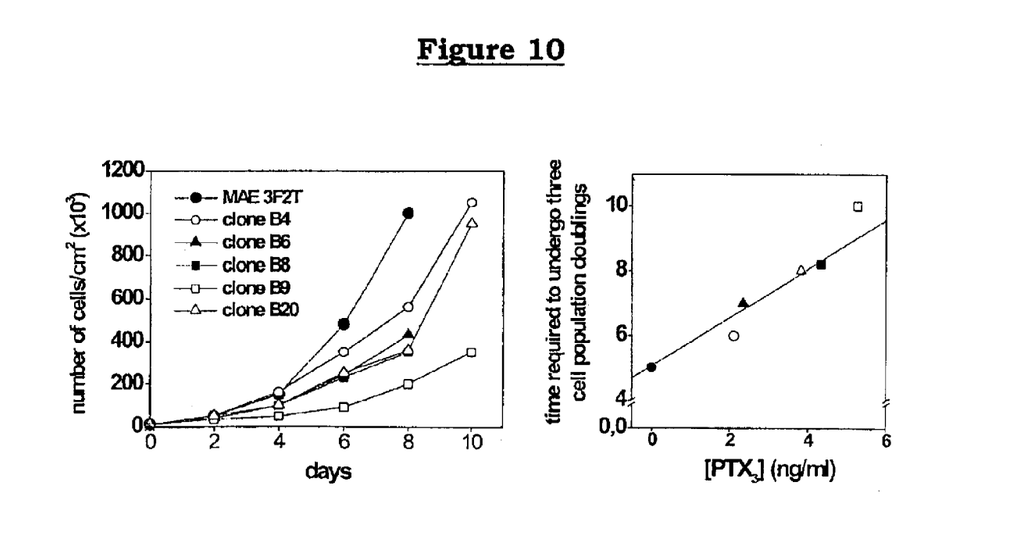
FIG. 10 shows that PTX3 over-expression inhibits FGF2MAE3F2T cells proliferation and that the extent of this inhibition correlates with the amount of PTX3produced by the different clones tested.

In details, several FGF2MAE3F2T, clones expressing different levels of PTX3 and parental FGF2MAE3F2T cells (that do not produce PTX3) were seeded at 10,000/cm$^2$ in 48-well plates in Dulbecco medium (DMEM) added with 10% FCS. After 24 h at 37° C., adherent cells were washed twice with DMEM without FCS and incubated for different period of time at 37° C. in DMEM containing 0.4% FCS. At the end of incubations cells were trypsinized and counted in a Burker chamber. Results reported in FIG. 10, shown that PTX3 over-expression inhibits FGF2MAE3F2T cells proliferation and that the extent of this inhibition correlates with the amount of PTX3 produced by the different clones tested.

Figure 11:
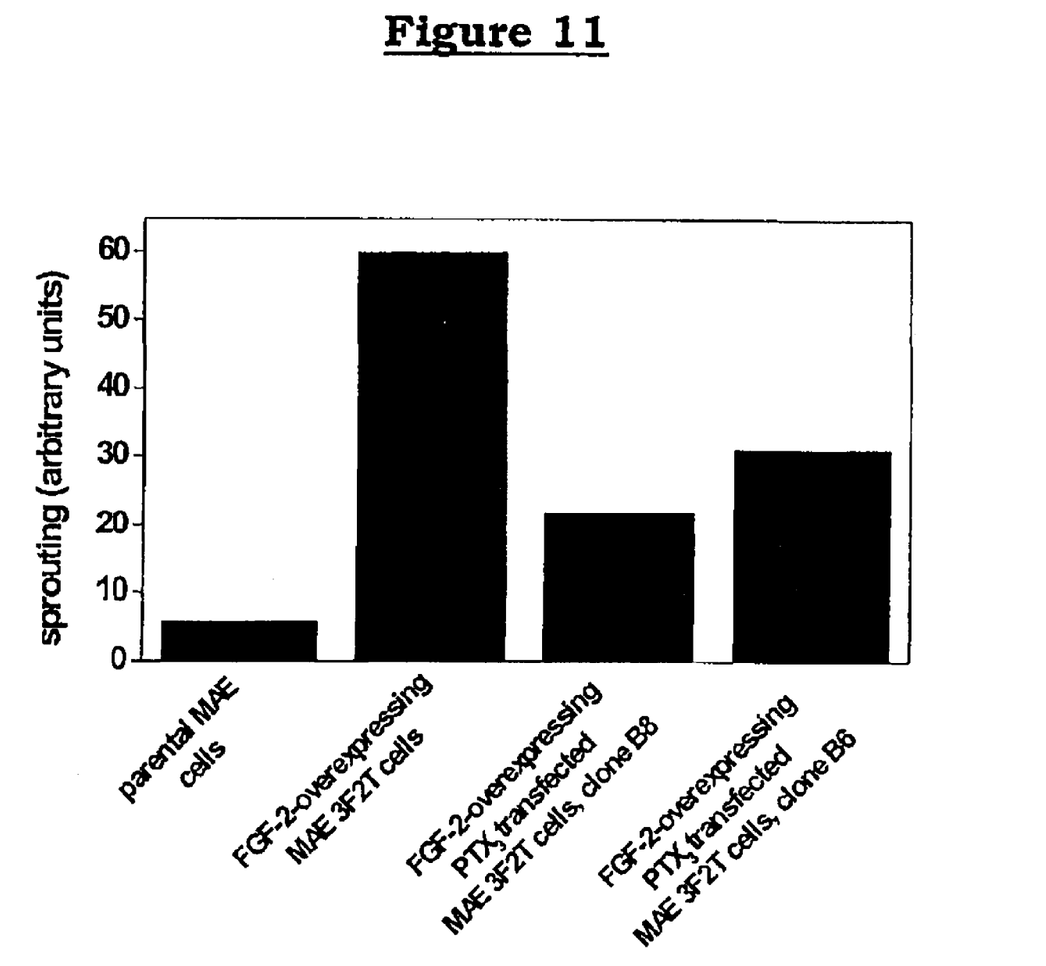
FIG. 11 shows that the invasive capacity of PTX3 overexpressing FGF2MAE3F2T clones is significantly lower that that of parental FGF2MAE3F2T cells.

To evaluate the invasive behaviour of FGF2MAE3F2T clones over-expressing PTX3 on three-dimensional fibrin gels, cell aggregates were prepared on agarose-coated plates exactly as described (Gualandris et al. 1996, Cell Growth Diff. 7:147-60). These aggregates were seeded onto fibrin-coated 48 well-plates. Immediately after seeding, 250 l of calcium-free medium containing fibrinogen (2.5 mg/ml) and thrombin (250 mU/ml) were added to each well and allowed to gel for 5 min at 37° C. Then, 500 l of culture medium were added on the top of the gel. In all the, experiments, the fibrinolytic inhibitor trasylol was added to the gel and to the culture medium at 200 KIU/ml to prevent the dissolution of the substrate. Formation of radially growing cell sprouts was evaluated after 2 days by computerized image analysis.

Results reported in FIG. 11 shown that the invasive capacity of PTX3 over-expressing FGF2MAE3F2T clones is significantly lower that that of parental FGF2MAE3F2T cells.

The results obtained demonstrate that PTX3 inhibits FGF-2 activity in endothelial cells when it is endogenously produced after gene transfer of its cDNA.

Thus, the compound according to the invention can be used in gene therapy protocols in accordance, to known methods (In Vivo. January-February 1998; 12(1):59-67; In Vivo. January-February 1998; 12(1):35'-41; In Vivo. November-December 1994; 8(5):771-80) for the treatment of diseases caused by an altered activation of the growth factor FGF-2.

The invention claimed is:

1. A method of treating a disease characterized by uncontrolled proliferation of fibroblasts or smooth muscle cells, wherein the disease is selected from the group consisting of cicatrization, restenosis after angioplasty, diabetic retinopathy, psoriasis and atherosclerosis; said method comprising administering full length human or mouse long pentraxin PTX3 to a person in need of said treatment.

2. The method of claim 1, wherein said full length human or mouse long pentraxin PTX3 is naturally occurring and administered to the person.

3. The method of claim 1, wherein said full length human or mouse long pentraxin PTX3 is a synthetic PTX3 made by recombinant or chemical means and administered to the person.

4. The method of claim 1, wherein full length human long pentraxin PTX3 is administered.

5. The method of claim 1, wherein cicatrization is treated.

6. The method of claim 1, wherein restenosis after angioplasty is treated.

7. The method of claim 1, wherein diabetic retinopathy is treated.

8. The method of claim 1, wherein psoriasis is treated.

9. The method of claim 1, wherein atherosclerosis is treated.

10. A method of treating a disease characterized by uncontrolled proliferation of fibroblasts or smooth muscle cells, wherein the disease is selected from the group consisting of cicatrization, restenosis after angioplasty, diabetic retinopathy, psoriasis and atherosclerosis; said method comprising administering a domain of human or mouse long pentraxin PTX3 which binds FGF-2 to a person in need of said treatment.

11. The method of claim 10, wherein cicatrization is treated.

12. The method of claim 10, wherein restenosis after angioplasty is treated.

13. The method of claim 10, wherein diabetic retinopathy is treated.

14. The method of claim 10, wherein psoriasis is treated.

15. The method of claim 10, wherein atherosclerosis is treated.

16. A method of treating a disease characterized by uncontrolled proliferation of fibroblasts or smooth muscle cells, wherein the disease is selected from the group consisting of cicatrization, restenosis after angioplasty, diabetic retinopathy, psoriasis and atherosclerosis; said method comprising administering a fragment of human or mouse long pentraxin PTX3 comprising its domain which binds FGF-2 to a person in need of said treatment.

17. The method of claim 16, wherein cicatrization is treated.

18. The method of claim 16, wherein restenosis after angioplasty is treated.

19. The method of claim 16, wherein diabetic retinopathy is treated.

20. The method of claim 16, wherein psoriasis is treated.

21. The method of claim 16, wherein atherosclerosis is treated.

* * * * *